United States Patent [19]

Kristensen et al.

[11] Patent Number: 5,476,667
[45] Date of Patent: Dec. 19, 1995

[54] METHOD FOR DRUG FORMULATION AND A PHARMACEUTICAL COMPOSITION

[75] Inventors: Arne Kristensen, Uppsala, Sweden; Per Holm, Vanløse, Denmark

[73] Assignee: Kabi Pharmacia AB, Uppsala, Sweden

[21] Appl. No.: 39,175

[22] PCT Filed: Oct. 15, 1991

[86] PCT No.: PCT/SE91/00690

§ 371 Date: Apr. 16, 1993

§ 102(e) Date: Apr. 16, 1993

[87] PCT Pub. No.: WO92/06679

PCT Pub. Date: Apr. 30, 1992

[30] Foreign Application Priority Data

Oct. 16, 1990 [SE] Sweden ................................ 9003296

[51] Int. Cl.⁶ ...................................................... A61K 9/14
[52] U.S. Cl. ........................... 424/489; 424/490; 424/497; 424/467
[58] Field of Search ............................ 242/467; 424/489, 424/490, 497; 427/3

[56] References Cited

U.S. PATENT DOCUMENTS

| | | | |
|---|---|---|---|
| 4,013,784 | 3/1977 | Speiser | 424/22 |
| 4,129,666 | 12/1978 | Wizerkaniuk | 427/3 |
| 4,132,753 | 1/1979 | Blichare et al. | 264/25 |
| 4,572,833 | 2/1986 | Pedersen et al. | 242/467 |
| 4,935,246 | 6/1990 | Ahrens | 424/490 |
| 4,957,746 | 9/1990 | Valducci | 424/490 |
| 5,147,655 | 9/1992 | Ibsen | 424/489 |

OTHER PUBLICATIONS

Drug Development And Industrial Pharmacy vol. 16, No. 8, 1990 T. Schaefer et al: "Melt granulation in a laboratory scale high shear mexer", pp. 1249–1277.

*Primary Examiner*—Thurman K. Page
*Assistant Examiner*—William E. Benston, Jr.
*Attorney, Agent, or Firm*—Birch, Stewart, Kolasch & Birch

[57] ABSTRACT

A melt granulating method for the production of pellets (spheres) which contain a therapeutically active substance of high-dosage type. The method is characterized by: (i) mechanically working a mixture which contains (a) the active substance in cohesive form and (b) a binder (melting point 40° C.–100° C.) while supplying sufficient energy for the binder to melt and to form spherical overwetted pellets; (ii) adding further cohesive substance, while maintaining the mechanical working; (iii) interrupting the mechanical working and supply of energy and cohesive substance when the desired mean particle size of dry pellets (spheres) has been achieved; and (iv) removing the smallest and largest particles and dividing the remaining pellets into dosage batches. A novel pharmaceutical composition containing a dosage of 300–500 mg of pellets is obtainable from this process.

23 Claims, No Drawings

METHOD FOR DRUG FORMULATION AND A PHARMACEUTICAL COMPOSITION

The present invention relates to a method (melt granulation) for producing pellets which contain a therapeutically active substance. The pellets produced have a spherical configuration. The invention is applicable primarily to high-dosage substances, i.e. compounds which shall be ingested per os in dosages of about 300–500 mg when administered to humans.

Pellets (e.g. spheres) intended for the administration of drugs per os are normally smaller than 2.5 mm (diameter) and larger than 0.3 mm, and are preferably in the range of 0.3–2.0 mm.

Melt granulation is a known process and involves mechanically working a particulate substance mixed with a binder which has a melting point of 40°–70° C., such as to form granules (pellets). During the process of manufacture, the binding agent melts and adheres to to the surface of the particulate substance, said particles therewith adhering together and building up to a granule form (pellets). Melt granulation will preferably result in matrix-type spherical pellets of low porosity. See, for instance, Drug. Dev. Ind. Pharm. 16 (1990), pages 1249–77. Melt granulation has been applied to the production of sustain release pellets, see U.S. Pat. Nos. 4,013,784; 4,132,753; and 4,935,246.

The most important pellet manufacturing methods are:

(1) Coating inert particles ("non-pareilles"=placebo pellets) with a solution that contains an active substances, binder and water. The amount of active substance used is normally </=30% (w/w) of the ultimate pellets. The method is primarily intended for active substances which are administered in dosages of 20–30 mg. The pellets obtained are spherical in shape when the particles used are spherical.

(2) Extrusion of a moist mass that contains active substance and an appropriate plastifying binder (e.g. 10–50% microcrystalline cellulose or methyl cellulose), followed by rounding the extrudate on a rotating disc. The amount of active substance present in pellets produced in accordance with this method is at maximum about 50% (w/w). This method produces primarily pellets of an elongated configuration.

(3) Coating crystals of active substance and auxiliary substances with suitable polymers. The geometric shape of the pellets obtained is determined by the geometric shape of the crystals. See for instance U.S. Pat. No. 4,957,746 or the corresponding EP publication 168,360.

When it is desired to release active substances in defined regions of the gastrointestinal tract, prepared pellets have been coated with a protective layer, for example a gastric-juice resistant film (enteric-coated), or have been placed in capsules that possess appropriate release properties.

None of these earlier known pelletizing methods have been found satisfactory for use with therapeutically active cohesive substances which are intended to be administered in high dosages and when quick release of the active substance from the administered pellet is desired subsequent to the pellets having reached their intended location in the gastrointestinal tract. The pellets produced have normally been excessively. small and/or have exhibited marked agglomeration tendencies. The pellets produced in accordance with the earlier known methods have also been too porous to enable the pellets to be converted to tablet form— more compact pellets have been desirable. There has been found the need for new methods of producing pellets, particularly pellets which contain water-soluble, therapeutically active substances of high dosage type.

The present invention provides one such method, which can also be applied to other therapeutically active substances. The inventive melt-granulating method (pelletizing) enables the production of a novel drug composition for active substances of high dosage type. This novel composition constitutes one aspect of the invention.

The inventive method for pelletizing a therapeutically active substance is characterized by:

(i) mechanically working a mixture which contains
   (a) the active substance in cohesive form and
   (b) a binder having a melting point between 40° C. and 100° C., preferably from 40° C. to 70° C., while supplying energy in an amount such that the binder will melt and the mixture will granulate to form spherical pellets, wherein the quantity ratio between active substance and binder is selected so that the spheroids formed will be overwetted;

(ii) adding further cohesive substance, either in one or more batches, optionally with the inclusion of intermediate binder additions while supplying energy during the mechanical working process so that the melting temperature of the binder is exceeded;

(iii) interrupting the mechanical working process, the supply of energy and the supply of cohesive substance and binder when the desired mean particle size of dry pellets (spheres) has been achieved, normally beneath 2.5 mm and preferably beneath 1 mm, such as beneath 0.8 mm, although always above 0.3 mm, such as above 0.4 mm; and (iv) removing particles which are larger or smaller than a predetermined maximum and minimum size respectively, optionally coating the remaining pellets (spheres) to impart thereto suitable release properties or stability properties, and grouping said remaining pellets into dosage batches each containing one dosage of the therapeutically active substance.

By cohesive substance is meant a particulate substance of poor flowability—interparticle forces give the particles a tendency to lump together or to agglomerate. The cohesiveness of a substance is often measured by its interface angle—substances which have a high angle of repose are cohesive. In principle, all substances having a mean particle size <30 μm, such as <20 μm, are cohesive.

Subsequent to melting the binder according to step (i) above and agitation has continued, the cohesive substance pelletizes normally instantaneously to form overwetted spheres. Continuous agglomerates of spheres are formed. Overwetting is necessary in the case of cohesive substances. The pellets formed are hard and cannot be deformed due to their low porosity and the strong interparticle bonds caused by the small particles of cohesive substance.

In step (ii), further cohesive substance is bound to the surface of the spheres formed in step (i). This enables agglomerates to be broken down.

The pellets (spheres) formed are of the matrix type, i.e. the particles of the cohesive substance are densely packed together in a matrix which consists of the binder. The porosity of the spheres is low, i.e. beneath 5% (pore volume in relation to the volume of the spheres).

The therapeutically active substances that can be pelletized in accordance with the invention normally consist of a therapeutically active compound which may be either water-soluble or water-insoluble. By water-soluble is meant that the compound will dissolve in the intended "fluid" in the gastrointestinal tract, i.e. in saliva and/or gastro and/or intestinal juices.

It is normally true that any compound which can be obtained in solid, particulate form at temperatures of up to about 393° K. can also be obtained as a cohesive substance. Large particles or lumps can be made cohesive by grinding and optionally by subjecting the material to spheronization and screening processes. Alternatively, a similar result can be achieved through the medium of freezing or spray-drying processes. The compounds in question are often salts (=ionic compounds), for example salts of azobis salicylic acid, particularly the 3,3'-isomer, acetylsalicylic acid, 5-aminosalicylic acid, 4-aminosalicylic acid, salicyl azosulfapyridine (sulfasalazine), or a penicillin salt, for example the calcium salt of penicillin V. If appropriate the carboxylic acid forms of these salts may also be used. The inventive method can also be applied to non-ionic compounds. The therapeutically active compounds concerned will normally have melting points higher than +120° C. (±15° C.). As previously mentioned, the compounds in question are primarily of the high dosage type.

The binder may have pronounced hydrophilic or lipophilic properties, to a greater or lesser degree. Mixtures of binders that possess mutually different properties may also be used. The melting point of the binder will preferably be higher than 40° C., preferably higher than 45° C. and lower 100° C., such as lower 70° C. The viscosity of the binder and also the contact angle (Danish grensfladevinkel) is of significance and both will preferably be low in order to enable the cohesive substance to be mixed uniformly. The viscosity of the binder at the process temperature used should be beneath 1000 cps (e.g. at 70° C.). Hydrophilic binders which are highly soluble or which are soluble to an unlimited degree in water are of particular interest for the manufacture of pellets from which the active substance will be quickly released. Examples in this regard are polyethylene glycol having a mean molecular weight $(M_w)$<7000 daltons, such as 1000–6000 daltons, for example an approximate molecular weight of 2000, 3000, 4000, 5000 or 6000 daltons. Lipophilic binders which are also hydrophilic to a greater or lesser degree are bees wax (pronouncedly lipophilic), glyceromonostearate, polyglycolglyceride (for example Celucire 50/13 (Gattefosse) having a melting point of 50° C. and HLB=13), polyoxyethylene stearate (for example PEG-40-stearate (Crodet 40) and PEG-100-stearate (Crodet 100), both having a melting point of 50° C. and a respective HLB of 16.9 and 18.8 (manufacturer, Croda Chemicals)), sorbitan esters (for example Span 60 having a melting point of 50° C. and an HLB=4.7).

The choice of binder is determined by the compound that is to be compacted and by the desired release properties of the resultant pellets. If the active compound is readily dissolved in aqueous media, for example in gastric juices (pH<6) or in saliva or in intestinal juices (pH=6-8) and it is desired that the active compound is released quickly in such a medium, there is chosen a hydrophilic water-soluble binder, such as polyethylene glycol according to the aforegoing. On the other hand, if it is desired that the active compound will be released more slowly, there is preferred a binder which has lower solubility in aqueous media, i.e. binding agents in which the lipophilic properties predominate.

The proportions in which binder/cohesive substance are used shall be such as to obtain overwetted pellets in step (i), i.e. the degree of saturation is above 100%. The terms "overwetted" and "degree of overwetting" are well known to the person skilled in this art and imply the addition of excess binder such as to cause the surfaces of the granules (spheres) obtained in step (i) to become tacky. The binder concentration should not be too high, since this would result in the formation of aggregates which will not separate to individual pellets (granules, spheres) in step (ii). The optimal proportion of binder:cohesive substance varies in dependence on the active compound (the compound as such, particle size and specific surface area of the particles, etc.), cohesiveness, binder and desired sphere size. As a general guideline, the active substance will normally be 60–95% (w/w), preferably 75–90% or 80–95% (w/w) of the resultant pellets, prior to optional aftertreatment (e.g. coating). Analogously, the quantity of binder used will be from 5 to 40% (w/w), preferably from 10–25% (w/w). Step (ii) enables the amount of active substance to be increased by 5–30% in comparison with the amount added in step (i).

The supply of energy to and mechanical working of the system is primarily achieved by agitation, wherein it is ensured that the amount of energy supplied will be sufficient to impart to the binder a viscosity suitable for granulating purposes. During the mechanical working process, the temperature shall always be allowed to rise above the melting temperature of the binder, although, as a rule, the temperature should always be kept beneath the melting point of the cohesive substance, suitably at least 10° C. beneath said melting point. This signifies that the temperature of the mixture being worked will normally be <140° C., such as <130° C. An excessively high supply of energy will facilitate baking of the mixture into large lumps, which is an obvious drawback. Energy supply by external heating methods may be problematic, since temperature gradients will readily occur in the mixture, resulting in inhomogenous granulation.

In the case of therapeutically active compounds which are soluble in water, the mechanical working process is, in principle, carried out in the absence of water. In some case small amounts of water may be advantageous, although not in amounts creating water solutions. The mechanical working process is preferably carried out in a so-called intensive mixer (=high shear mixer), i.e. a mixer of the type described in Danish Patent Application No. 3290/89. The mixer retailed under the name PELLMIX by NIRO ATOMIZER A/S (Soeborg, Denmark) is of particular interest in this connection.

The size in which the pellets are obtained is determined by such process variables as the particle size of the cohesive substance used, the binder used, the mechanical working process applied, the agitation rate, the mixing vessel used and/or the geometric configuration of the agitator, and surface coating, temperature, etc. Process parameters which will result in a given pellet size with a given binder and a given cohesive substance are determined empirically, as illustrated in the experimental part of this specification. In order to obtain an acceptable yield, the process parameters are preferably adapted so as to obtain a particle distribution <75% pellets (spheres) in a range ±0.5 mm, preferably ±0.3 mm, around a given value of the diameter in the pellet range mentioned in the introduction.

Sieving, or screening, is effected in a known manner to recover a suitable fraction having a size which lies within the aforesaid pellet range, preferably a size of 0.3–1.5 mm.

According to one aspect, the invention is a pharmaceutical composition which contains pellets that provide one dosage of the therapeutically active compound. According to the invention, the pellets used are characterized in that they are spherical and of the matrix type and contain cohesive substance and binder of the aforesaid kind and in the aforesaid quantities.

The inventive pellets (spheres) can be enteric-coated in a known manner, such that the active substance will be released in the intestine. The spheres may also be disposed in capsules, which may also be resistant to gastric juices.

Different embodiments of the invention are defined in the accompanying claims, which form part of the descriptive portion of this specification.

EXPERIMENTAL PART

PART 1. The invention applied on PcV-K (Phenoxy methyl penicillin calcium; Fermenta Sweden)

Apparatus: Pellmix 50 liter (Niro Atomizer A/S, Soeborg, Denmark).

Starting point: The following experiments were based on introductory studies carried out in a 6-liter intensive mixer, wherewith we found that an optimum composition was melt pelletizing of 22% polyethylene glycol 3000 (PEG) with 78% calcium salt of penicillin V (=PcV-K) and subsequent dry addition of PcV-K.

Experiment 1.1:

8500 g PcV-K and 1870 g PEG 3000. Dry substance addition (PcV-K) 1×2000 g+500 g. Agitator speed 600 rpm. Evaluation: The PEG melted after about 15 minutes (59° C.), whereafter the temperature was increased to 100° C. after a further 5 minutes. The product became overwetted at about 125° C. and 2000 g of dry substance were added, followed by a further 500 g within some few minutes. The product consisted of large lumps, 2–5 cm, and pellets (spheres) of the correct size. Screen analysis: 1.1.

Experiment 1.2:

The starting composition and the addition of dry substance (PcV-K) were in accord with Experiment 1.1. The agitator speed was initially 600 rpm. Evaluation: In order to achieve a lower rise in temperature, the agitator speed was reduced to 500 rpm subsequent to having reached the melting point of PEG (59° C.). The final temperature was 110° C. Evaluation: The product had a broad particle distribution, including "fines" (fine particulate material) and large pellets having a diameter of from 5 to 10 mm.

Experiment 1.3:

8500 g PcV-K and 2040 g PEG 3000. The agitator speed was 600 rpm (start). Evaluation: Because of overwetting problems relatively early on in the process, the agitator speed was reduced to 200 rpm (116° C.), which resulted in controlled growth.

Experiment 1.4:

The starting composition was the same as that used in Experiment 1.1. The dry substance addition (PcV-K) was 3×700 g. The agitator speed was initially 600 rpm. Evaluation: The agitator speed was lowered to 300 rpm, at temperature 70° C. The rise in temperature from 70° C. to 90° C. took 16 minutes. Dry substance was added when the temperature had reached 90° C. Screen analysis: 1.4.

Experiment 1.5:

The starting composition was the same as that used in Experiment 1.1. The dry substance addition (PcV-K) was 2×1000 g+1×300 g. The agitator speed was initially 600 rpm. Evaluation: The agitator speed was lowered to 400 rpm at temperature 70° C. The rise in temperature from 70° C. to 90° C. took about 6 minutes. Dry substance was added when the temperature was 100° C. Screen analysis: 1.5.

Experiment 1.6:

8500 g PcV-K and 1700 g PEG 3000 (20%). The dry substance addition (PcV-K) was 2×1000 g+1×300 g. The agitator speed was initially 600 rpm. Evaluation: The process conditions were the same as those in Experiment 1.10. The amount of PEG used was insufficient for the substance (PcV-K) to be pelletized. The total PEG-concentration (17.3% PEG) was lower than the corresponding concentration in Experiment 1.5.

Experiment 1.7:

8500 g PcV-K and 1785 g PEG 3000 (21%). The process conditions were analogous with the process conditions of Experiment 1.5. Screen analysis: 1.7.

Experiment 8:

8500 g PcV-K and 1828 g PEG 3000 (21.5%). The process conditions were analogous with those used in Experiment 1.5.

Experiment 9:

This experiment was analogous with Experiment 1.8, with the exception of the level to which the agitator speed was lowered. Evaluation: The agitator speed was lowered to 500 rpm at temperature 70° C. The rise in temperature from 70° to 90° C. took about 3 minutes. The dry substance charges were added at a temperature of about 125° C., at intervals of some few minutes. Screen analysis: 1.9.

Experiment 1.10:

The experiment was analogous with Experiment 1.8, with the exception of the value to which the agitator speed was lowered. Evaluation: The agitator speed was lowered to 450 rpm at a temperature of 60° C., and dry substance added. Screen analysis: 1.10.

PART 1. CONCLUSION

PEG: The experiments show that it is possible to obtain pellets of suitable size when PEG is present in the starting mixture in a concentration of 21–22%. The experiments also show that a lower percentile addition will not result in pelletization and that a higher percentile addition will result in the formation of large lumps. TEMPERATURE: Since there is found a relationship between agitator speed and temperature, it is difficult to maintain the temperature at a reasonable level of about 110° C. (maximum temperature for the system tested). Experiment 4 shows that pelletization can be achieved beneath 100° C.

PART 2. The invention applied to 3,3'-diazo-bissali-cylic acid (DIPENTUM, Pharmacia AB, Sweden)

Apparatus: Intensive mixer PELLE (Niro Atomizer A/S, Soeborg, Denmark).

Melt pelletization of 3,3'-diazo-bissalicylic acid (mean particle size 4 μm) with PEG 3000 or glycerol monostearate as binder.

Experiment 2.1:

800 g DIPENTUM and 160 g PEG 3000 (20%). The agitator was run at a speed of 1200 rpm until the PEG addition melted, and thereafter 900 rpm. Dry substance addition 3×80 g DIPENTUM. Jacket temp. 55° C. (external heating). Large fraction <0.700 mm. Screen analysis: 2.1.

Experiment 2.2:

The process conditions were the same as those in Experiment 2.1, with the exception that a smaller quantity of PEG 3000 was used (147 g, 18.3%). Pellets formed after a long process time and after the melting point of PEG had been reached.

Experiment 2.3:

Process conditions were the same as those in Experiment 2.1, but with the difference that smaller quantity of PEG 3000 (153 g, 19.2%) was used. The size distribution was analogous with Experiment 2.1. Screen analysis: 2.3.

Experiment 2.4:

Process conditions were the same as those in Experiment 2.1, with the exception of an addition of 10% Avicel PH 10 (80 g) and 720 g DIPENTUM. The particle size was larger than that obtained in Experiment 2.1 and 2.3. Screen analysis: 2.4.

Experiment 2.5:

800 g DIPENTUM and 152 g glycerol monostearate (19%). The agitator speed was maintained at 1100 rpm until the PEG added to the system melted. The speed was then lowered to 900 rpm. Dry substance addition 2×80 g DIPENTUM. Jacket temp. 55° C. (external heating). Overwet product.

Experiment 2.6:

The process conditions were the same as those in Experiment 2.5, with the exception of a smaller quantity of glycerol monostearate 128 g (16%). Screen analysis: 2.6.

Experiment 2.7:

The process conditions were the same as those in Experiment 2.6, except for an addition of 9 g sodium lauryl sulphate 8 g. Dissolution tests carried out on 100 mg pellets, USP paddle 100 rpm (37° C.) in distilled water resulted in 90% dissolution after 80 minutes. In the absence of sodium lauryl sulphate, a 90% dissolution was achieved after 120 minutes.

Experiment 2.8:

The process conditions were the same as those in Experiment 2.5, but with a melt binder which comprised a mixture of PEG 3000 and glycerol monostearate (1:1), total 140 g. A dissolution test analogous with Test 2.7 resulted in about 90% dissolution after 40 minutes. A dissolution of 90% was achieved after 120 minutes in the absence of sodium lauryl sulphate.

SCREEN ANALYSES

| Screen Analysis 1.1 | | | Screen Analysis 1.4 | |
|---|---|---|---|---|
| Analysis weight in grams: 100.0 | | | 135.20 | |
| Diam. μm | W. % | Cum. % | W. % | Cum. % |
| 10 | | | 0.1 | 0.1 |
| 75 | | | 0.1 | 0.1 |
| 125 | 0.1 | 0.1 | 0.2 | 0.4 |
| 180 | 0.0 | 0.1 | 0.7 | 1.0 |
| 250 | 0.2 | 0.3 | 2.7 | 3.7 |
| 355 | 1.1 | 1.4 | 6.0 | 9.7 |
| 500 | 4.2 | 5.6 | 9.7 | 19.4 |
| 710 | 24.9 | 30.5 | 28.5 | 47.9 |
| 1000 | 62.5 | 93.0 | 38.5 | 86.3 |
| 1400 | 7.0 | 100.0 | 13.7 | 100.0 |
| Mean diam. DGW: 1065.0 μm | | | 935.4 μm | |
| Sread SGW: 1.29 | | | 2.56 | |

| Screen Analysis 1.5 | | | Screen Analysis 1.7 | |
|---|---|---|---|---|
| Analysis weight in grams: 133.50 | | | 121.20 | |
| Diam. μm | W. % | Cum. % | W. % | Cum. % |
| 250 | 0.7 | 0.7 | 0.3 | 0.3 |
| 355 | 4.8 | 5.5 | 4.4 | 4.7 |
| 500 | 21.7 | 27.3 | 27.8 | 32.5 |
| 710 | 42.9 | 70.2 | 42.5 | 75.0 |
| 1000 | 24.4 | 94.6 | 20.1 | 95.1 |
| 1400 | 5.4 | 100.0 | 4.9 | 100.0 |
| Mean diam. DGW: 845.7 μm | | | 819.0 μm | |
| Spread SGW: 1.39 | | | 1.38 | |

| Screen Analysis 1.9 | | | Screen Analysis 1.10 | |
|---|---|---|---|---|
| Analysis weight in grams: 127.30 | | | 116.00 | |
| Diam. μm | W. % | Cum. % | W. % | Cum. % |
| 180 | 0.1 | 0.1 | 0.1 | 0.1 |
| 250 | 0.9 | 1.0 | 0.8 | 0.9 |
| 355 | 9.4 | 10.4 | 10.1 | 10.9 |
| 500 | 40.6 | 51.1 | 41.0 | 52.0 |
| 710 | 37.9 | 88.9 | 37.4 | 89.4 |
| 1000 | 9.4 | 98.4 | 9.4 | 98.8 |
| 1400 | 1.6 | 100.0 | 1.2 | 100.0 |
| Mean diam. DGW: 708.3 μm | | | 703.0 μm | |
| Spread SGW: 1.36 | | | 1.35 | |

| Screen Analysis 2.1 | | | Screen Analysis 2.3 | |
|---|---|---|---|---|
| Analysis weight in grams: 94.40 | | | 54.40 | |
| Diam. μm | W. % | Cum. % | W. % | Cum. % |
| 75 | 0.1 | 0.1 | | |
| 125 | 0.0 | 0.1 | | |
| 180 | 0.6 | 0.7 | 3.1 | 3.1 |
| 250 | 2.6 | 3.4 | 2.9 | 6.1 |
| 355 | 10.4 | 13.8 | 5.0 | 11.0 |
| 500 | 29.1 | 42.9 | 24.8 | 35.8 |
| 710 | 35.7 | 78.6 | 41.4 | 77.2 |
| 1000 | 17.2 | 95.8 | 17.5 | 94.7 |
| 1400 | 3.2 | 98.9 | 1.3 | 96.0 |
| 2000 | 0.4 | 99.5 | 0.4 | 96.3 |
| 2830 | 0.2 | 99.6 | 3.5 | 99.8 |
| 4000 | 0.4 | 100.0 | 0.2 | 100.0 |
| Mean diam. DGW: 743.9 μm | | | 782.6 μm | |
| Spread SGW: 1.49 | | | 1.63 | |

| Screen Analysis 2.4 | | | Screen Analysis 2.6 | |
|---|---|---|---|---|
| Analysis weight in grams: 86.90 | | | 107.6 | |
| Diam. μm | W. % | Cum. % | W. % | Cum. % |
| 75 | 0.1 | 0.1 | 0.1 | 0.1 |
| 125 | 0.1 | 0.2 | 0.0 | 0.1 |
| 180 | 0.1 | 0.3 | 0.0 | 0.1 |
| 250 | 0.0 | 0.3 | 0.1 | 0.2 |
| 355 | 2.5 | 2.9 | 2.9 | 3.1 |
| 500 | 22.6 | 25.4 | 9.0 | 12.1 |
| 710 | 32.6 | 58.0 | 39.1 | 51.2 |
| 1000 | 23.4 | 81.4 | 38.2 | 89.4 |
| 1400 | 16.8 | 98.2 | 9.3 | 98.7 |
| 2000 | 0.6 | 98.7 | 0.7 | 99.4 |
| 2830 | 0.2 | 99.0 | 0.2 | 99.6 |
| 4000 | 1.0 | 100.0 | 0.4 | 100.0 |
| Mean diam. DGW: 934.0 μm | | | 979.1 μm | |
| Spread SGW: 1.49 | | | 1.39 | |

We claim:

1. A melt granulating method for producing pellets which contain a therapeutically active substance, comprising, in an intensive mixer, (i) mechanically working a mixture which contains (a) the active substance in cohesive form and (b) a binder having a melting point between 40° C. and 100° C. while supplying energy in an amount such that the binder will melt and the mixture will granulate to form pellets, wherein the quantity ratio between active substance and binder is selected so that the pellets formed will be overmoist so as to become tacky;

(ii) adding further cohesive substance, either in one or more batches, while supplying energy during the mechanical working process so that the melting temperature of the binder is exceeded;

(iii) interrupting the mechanical working involving the supply of energy and the supply of the cohesive substance and the binder when the desired mean particle size of dry pellets has been achieved, and (iv) removing particles which are larger or smaller than a predetermined maximum and minimum size respectively.

2. A method according to claim 1, wherein the therapeutically active substance is a water-soluble compound.

3. A method according to claims 1 or 2 wherein the binder is hydrophilic.

4. A method according to claim 1 wherein the pellets obtained are divided into dosages of 300–500 mg active substance.

5. A method according to claim 1 wherein the mechanical working is produced by agitation.

6. A method according to claim 1 wherein the temperature is maintained below 120° C. during the mechanical working.

7. A method according to claim 1 wherein the binder is a polyethylene glycol.

8. A method according to claim 1 wherein the therapeutically active substance is in the form of a salt.

9. A pharmaceutical composition containing a dosage of a pelletized cohesive active substance in the form of particles having a mean particle size below 20 μm, comprising pellets containing the active substance and a water-soluble binder having a melting temperature of 40°–100° C., wherein the active substance constitutes 60–95% (w/w) and the binder 5–40% (w/w) of the pellets.

10. The melt granulating method of claim 1 wherein the binder has a melting point from 40° C. to 70° C.

11. The melt granulating method of claim 1 wherein the pellets are spherical.

12. The melt granulating method of claim 1 wherein intermediate binder additions are included with the cohesive substances of step (ii).

13. The melt granulating method of claim 1 wherein the mean particle size of dry pellets is less than 2.5 mm.

14. The melt granulating method of claim 1 wherein the mean particle size of the dry pellets is less than 1 mm.

15. The melt granulating method of claim 1 wherein the mean particle size of the dry pellets is less than 0.8 mm but greater than 0.3 mm.

16. The melt granulating method of claim 1 wherein the mean particle size of the dry pellets is less than 0.8 mm but greater than 0.4 mm.

17. The melt granulating method of claim 1 wherein the pellets remaining following step (iv) are enteric coated which pellets are then grouped into dosage batches each containing one dosage of the therapeutically active substance.

18. The method according to claim 8 wherein the salt is a member selected from the group consisting of azobissalicylic acid, acetylsalicylic acid, 5-amino-salicylic acid, salicylazosulfapyridine, or a penicillin salt.

19. A pharmaceutical composition according to claim 9 wherein the particles have a mean particle size less than 20 μm.

20. The method according to claim 18 wherein the penicillin salt is the calcium salt of penicillin V.

21. A melt granulating method for producing pellets which contain a therapeutically active substance, comprising, in an intensive mixer, (i) stirring a mixture which contains (a) the active substance in cohesive form and (b) a binder having a melting point between 40° C. and 100° C. while heating in an amount such that the binder will melt and the mixture will granulate to form pellets, wherein the quantity ratio between active substance and binder is selected so that the pellets formed will be overmoist so as to become tacky;

(ii) adding further cohesive substance, either in one or more batches, while heating during the stirring process so that the melting temperature of the binder is exceeded;

(iii) interrupting the stirring involving the heating and the supply of the cohesive substance and the binder when the desired mean particle size of dry pellets has been achieved, and (iv) removing particles which are larger or smaller than a predetermined maximum and minimum size respectively.

22. The melt granulating method of claim 21 wherein the pellets remaining following step (iv) are enteric coated which pellets are then grouped into dosage batches each containing one dosage of the therapeutically active substance.

23. A method according to claim 1, wherein the pellets remaining after step (iv) contain the active substance in an amount of 60–95% (w/w) and the binder in an amount of 5–40% (w/w).

* * * * *